United States Patent
Goget et al.

(10) Patent No.: US 8,628,586 B2
(45) Date of Patent: Jan. 14, 2014

(54) COMPOSITION COMPRISING AN OXIDATION DYE PRECURSOR, A POLYCONDENSATE OF ETHYLENE OXIDE AND PROPYLENE OXIDE AND A CATIONIC POLYMER WITH A CHARGE DENSITY OF GREATER THAN OR EQUAL TO 4 MEQ./G

(75) Inventors: Caroline Goget, Paris (FR); Katia Dutheil-Gouret, Les Metairies (FR); Ludivine Masselin, Paris (FR); Marika Fila, Courbevoie (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/992,303

(22) PCT Filed: Dec. 7, 2011

(86) PCT No.: PCT/EP2011/071988
§ 371 (c)(1),
(2), (4) Date: Jun. 27, 2013

(87) PCT Pub. No.: WO2012/076559
PCT Pub. Date: Jun. 14, 2012

(65) Prior Publication Data
US 2013/0305464 A1 Nov. 21, 2013

Related U.S. Application Data

(60) Provisional application No. 61/426,313, filed on Dec. 22, 2010.

(30) Foreign Application Priority Data

Dec. 7, 2010 (FR) ...................... 10 60199

(51) Int. Cl.
*A61Q 5/10* (2006.01)
(52) U.S. Cl.
USPC ................ 8/405; 8/406; 8/408; 8/410; 8/412; 8/424; 8/435; 8/552; 8/554; 8/555
(58) Field of Classification Search
USPC ............. 8/405, 406, 408, 410, 412, 424, 435, 8/552, 554, 555
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 3,206,462 A | 9/1965 | McCarty | |
| 3,874,870 A | 4/1975 | Green et al. | |
| 3,910,862 A | 10/1975 | Barabas et al. | |
| 3,912,808 A | 10/1975 | Sokol | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,075,136 A | 2/1978 | Schaper | |
| 4,165,367 A | 8/1979 | Chakrabarti | |
| RE30,199 E | 1/1980 | Rose et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,579,732 A | 4/1986 | Grollier et al. | |
| 4,608,250 A | 8/1986 | Jacquet et al. | |
| 4,719,099 A | 1/1988 | Grollier et al. | |

(Continued)

FOREIGN PATENT DOCUMENTS

| | | |
|---|---|---|
| DE | 23 59 399 | 6/1975 |
| DE | 38 43 892 | 6/1990 |

(Continued)

OTHER PUBLICATIONS

STIC Search Report dated Aug. 12, 2013.*
International Search Report for PCT/EP2011/071988.
Edens, Michael W., et al., "Applications of Block Copolymer Surfactants," Developments in Block Copolymer Science and Technology, Wiley & Sons, Ltd., Jan. 2004 (XP-001233807), pp. 326-340.

*Primary Examiner* — Eisa Elhilo
(74) *Attorney, Agent, or Firm* — O'Brien Jones, PLLC.

(57) ABSTRACT

The present invention relates to a dye composition comprising at least one oxidation dye precursor, at least one polycondensate of ethylene oxide and propylene oxide having the following structure: H—(O—CH$_2$—CH$_2$)$_a$—(O—CH(CH$_3$)—CH$_2$)$_b$—(O—CH$_2$—CH$_2$)$_{a'}$—OH, in which a and a' range from 2 to 150 and b ranges from 1 to 100; and at least one cationic polymer with a charge density of greater than or equal to 4 meq./g. The invention also relates to a dyeing process using this composition after mixing with a composition comprising an oxidizing agent. Another subject of the invention is devices comprising at least two compartments, the first compartment comprising the above composition and the second compartment comprising a composition comprising at least one oxidizing agent.

20 Claims, No Drawings

(56) References Cited

U.S. PATENT DOCUMENTS

| | | | |
|---|---|---|---|
| 4,777,040 A | 10/1988 | Grollier et al. | |
| 4,839,166 A | 6/1989 | Grollier et al. | |
| 4,948,579 A | 8/1990 | Jacquet et al. | |
| 4,970,066 A | 11/1990 | Grollier et al. | |
| 4,996,059 A | 2/1991 | Grollier et al. | |
| 5,009,880 A | 4/1991 | Grollier et al. | |
| 5,057,311 A | 10/1991 | Kamegai et al. | |
| 5,061,289 A | 10/1991 | Clausen et al. | |
| 5,089,252 A | 2/1992 | Grollier et al. | |
| 5,196,189 A | 3/1993 | Jacquet et al. | |
| 5,380,340 A | 1/1995 | Neunhoeffer et al. | |
| 5,534,267 A | 7/1996 | Neunhoeffer et al. | |
| 5,554,197 A | 9/1996 | Assini et al. | |
| 5,663,366 A | 9/1997 | Neunhoeffer et al. | |
| 5,766,576 A | 6/1998 | Lowe et al. | |
| 5,958,392 A | 9/1999 | Grollier et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,692,539 B2 | 2/2004 | Desenne et al. | |
| 6,695,887 B2 * | 2/2004 | Cottard et al. | 8/405 |
| 6,730,789 B1 | 5/2004 | Birault et al. | |
| 2002/0010970 A1 | 1/2002 | Cottard et al. | |
| 2002/0050013 A1 | 5/2002 | Vidal et al. | |
| 2002/0184717 A9 | 12/2002 | Cottard et al. | |
| 2003/0019051 A9 | 1/2003 | Vidal et al. | |
| 2003/0172473 A1 | 9/2003 | Desenne et al. | |
| 2004/0163186 A1 | 8/2004 | Simonet et al. | |
| 2008/0104775 A1 | 5/2008 | Simonet et al. | |
| 2009/0211036 A1 | 8/2009 | Ascione | |

FOREIGN PATENT DOCUMENTS

| | | |
|---|---|---|
| DE | 41 33 957 | 4/1993 |
| DE | 195 43 988 | 5/1997 |
| EP | 0 080 976 | 6/1983 |
| EP | 0 122 324 | 10/1984 |
| EP | 0 337 354 | 10/1989 |
| EP | 0 548 620 | 6/1993 |
| EP | 1 329 216 | 7/2003 |
| EP | 1 426 040 | 6/2004 |
| EP | 2 092 933 | 8/2009 |
| FR | 2 077 143 | 10/1971 |
| FR | 2 080 759 | 11/1971 |
| FR | 2 190 406 | 2/1974 |
| FR | 2 270 846 | 12/1975 |
| FR | 2 316 271 | 1/1977 |
| FR | 2 320 330 | 3/1977 |
| FR | 2 336 434 | 7/1977 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 519 863 | 7/1983 |
| FR | 2 598 611 | 11/1987 |
| FR | 2 733 749 | 11/1996 |
| FR | 2 801 308 | 5/2001 |
| FR | 2 803 196 | 7/2001 |
| FR | 2 886 136 | 12/2006 |
| GB | 1026978 | 4/1966 |
| GB | 1153196 | 5/1969 |
| GB | 1546809 | 5/1979 |
| JP | 02-019576 | 1/1990 |
| JP | 05-163124 | 5/1993 |
| WO | 94/08969 | 4/1994 |
| WO | 94/08970 | 4/1994 |
| WO | 96/15765 | 5/1996 |

* cited by examiner

COMPOSITION COMPRISING AN OXIDATION DYE PRECURSOR, A POLYCONDENSATE OF ETHYLENE OXIDE AND PROPYLENE OXIDE AND A CATIONIC POLYMER WITH A CHARGE DENSITY OF GREATER THAN OR EQUAL TO 4 MEQ./G

This is a national stage application of PCT/EP2011/071988, filed internationally on Dec. 7, 2011, which claims priority to U.S. Provisional Application No. 61/426,313, filed on Dec. 22, 2010; as well as French Application FR 1060199, filed on Dec. 7, 2010.

The present invention relates to a composition for dyeing human keratin fibres, especially the hair. The invention also relates to a dyeing process using this composition, and to a multi-compartment device containing it.

Among the methods for dyeing human keratin fibres, such as the hair, mention may be made of oxidation dyeing or permanent dyeing. More particularly, this dyeing method uses one or more oxidation dye precursors and usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, when combined with oxidizing products, can give access to coloured species.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

It is also possible to add to these compositions direct dyes, which are coloured, and colouring molecules that have affinity for fibres. The direct dyes generally used are chosen from nitrobenzene, anthraquinone, nitropyridine, azo, methine, azomethine, xanthene, acridine, azine and triarylmethane direct dyes. The presence of such compounds enables the obtained coloration to be further enriched with tints or enables the chromaticity of the obtained coloration to be increased.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloration, via an oxidative condensation reaction between the oxidation dyes.

The oxidation dye must moreover satisfy a certain number of requirements. Thus, it must be free of toxicological drawbacks, it must enable shades to be obtained in the desired intensity and it must show the resistance to external attacking factors such as light, bad weather, washing, permanent waving, or aspiration and rubbing.

The dyes must also be able to cover grey hair and, finally, they must be as unselective as possible, i.e. they must produce the smallest possible colour differences along the same keratin fibre, which generally comprises areas that are differently sensitized (i.e. damaged) from its end to its root.

It is common practice to use dye compositions containing particular polymers for the purpose of stabilizing the composition and maintaining its viscosity, in order to keep the dye composition on the hair during the time of reaction/penetration of the dyes into the keratin fibre and to limit the risks of running onto the face.

It has moreover been recommended to use surfactants, in particular nonionic surfactants, in oxidation dyeing and especially in dyeing products that are in the form of liquids containing oxidation dye precursors to be mixed with oxidizing compositions, liquid compositions in which the proportions of these surfactants are often large. To obtain satisfactory application conditions after mixing these liquid compositions with the oxidizing compositions, especially with a viscosity that is sufficient to prevent running, it most often proves necessary to thicken slightly the said liquid compositions. Unfortunately, the majority of thickening polymers lead to rapid demixing of the composition. Moreover, very often, the viscosity-increasing power of the polymers is very greatly reduced when they are combined with relatively large amounts of surfactants.

One of the aims of the present invention is to obtain a composition for dyeing the hair, which is stable over time and which remains on the hair during application, without running, while at the same time conserving the dyeing properties obtained on the hair, in particular conserving powerful, chromatic and uniform colorations between the end and the root of the same fibre and from one fibre to another.

This aim is achieved by the present invention, one subject of which is a dye composition comprising at least one oxidation dye precursor and at least one polycondensate of ethylene oxide and propylene oxide, of formula (I) below:

$$H-(O-CH_2-CH_2)_a-(O-CH(CH_3)-CH_2)_b-(O-CH_2-CH_2)_{a'}-OH, \quad (I)$$

in which a and a' range from 2 to 150 and b ranges from 1 to 100; and at least one cationic polymer with a charge density of greater than or equal to 4 meq./g.

The invention also relates to a hair dyeing process that consists in applying to the fibres the composition of the invention, in the presence of an oxidizing agent.

A subject of the invention is also a two-compartment device containing, in one of the compartments, the composition of the invention as defined above and, in the other compartment, a composition comprising at least one oxidizing agent.

Thus, the invention makes it possible to obtain a thickened composition that is stable over time, which remains in place after application on the hair, without the risk of running. In addition, this composition has improved dyeing properties.

In the description, the term "at least one" associated with an ingredient of the composition is equivalent to "one or more".

The composition according to the invention contains at least one polyethylene glycol/polypropylene glycol/polyethylene glycol triblock polycondensate. In the chemical structure described above, preferably, a and a' range from 10 to 130 and b ranges from 20 to 80, better still a and a' range from 50 to 130 and b ranges from 30 to 80, and even better still a and a' range from 80 to 130 and b ranges from 40 to 80. According to one particular embodiment, a and a' are identical.

The polycondensate of ethylene oxide and of propylene oxide that is useful in the composition of the invention preferably has a weight-average molecular weight ranging from 250 to 19 000, better still ranging from 1200 to 15 000, in particular ranging from 1500 to 10 000 and even better still ranging from 1500 to 5000.

Advantageously, the said polycondensate of ethylene oxide and propylene oxide has a cloud point, at 10 g/l in distilled water, of greater than or equal to 20° C. and preferably of greater than or equal to 60° C. The cloud point is measured according to standard ISO 1065.

As polycondensates of ethylene oxide and propylene oxide that may be used according to the invention, mention may be made of the polyethylene glycol/polypropylene glycol/polyethylene glycol triblock polycondensates sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184), Synperonic® PE/F88 (INCI name: Poloxamer 238), Synperonic® PE/F87 (INCI name: Poloxamer 237) from the company Croda, or Lutrol® F68 (INCI name: Poloxamer 188) from the company BASF.

According to one embodiment of the invention, the amount of polycondensates of ethylene oxide and propylene oxide preferably ranges from 0.1% to 20% by weight, even more preferentially from 0.5% to 10% by weight and better still from 1% to 5% by weight relative to the total weight of the composition.

The oxidation dyes that are useful in the composition of the invention are generally chosen from oxidation bases and couplers.

Examples of oxidation bases that may be mentioned include para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(3-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methyl-pyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazino-pyrazole, 1-benzyl-4,5-diamino-3-methylpyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used. A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferably be used as heterocyclic bases.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(1-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, β-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(f-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]-benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

According to one embodiment, the composition comprises at least one oxidation base and optionally a coupler.

The oxidation base(s) each advantageously represent from 0.0001% to 10% by weight relative to the total weight of the composition, and preferably from 0.005% to 5% by weight relative to the total weight of the composition.

The content of coupler(s), if it is (they are) present, each advantageously represent from 0.0001% to 10% by weight relative to the total weight of the composition, and preferably from 0.005% to 5% by weight relative to the total weight of the composition.

The composition of the invention contains at least one cationic polymer with a charge density of greater than or equal to 4 milliequivalents per gram (meq./g), preferably greater than or equal to 5 milliequivalents per gram (meq./g), preferably ranging from 5 to 20 meq./g and more particularly from 5.5 to 10 meq./g.

The cationic charge density of a polymer corresponds to the number of moles of cationic charges per unit mass of polymer under conditions in which it is totally ionized. It may be determined by calculation if the structure of the polymer is known, i.e. the structure of the monomers constituting the polymer and their mole proportion or weight proportion. It may also be determined experimentally via the Kjeldahl method, generally at a pH of about 7 at room temperature.

The cationic polymers with a cationic charge density of greater than 4 meq./g, which may be used in accordance with the present invention, may be chosen from any polymer known per se as improving the cosmetic properties of hair treated with compositions, i.e. especially those described in patent application EP-A-0 337 354 and in French patent applications FR-A-2 270 846, 2 383 660, 2 598 611, 2 470 596 and 2 519 863.

In general, for the purposes of the present invention, the term "cationic polymer" denotes any polymer comprising cationic groups and/or groups that may be ionized into cationic groups.

The cationic polymers are chosen from those containing units comprising primary, secondary, tertiary and/or quaternary amine groups that either may form part of the main polymer chain or may be borne by a side substituent directly attached thereto.

The cationic polymers used generally have a number-average molar mass of between 500 and $5 \times 10^6$ approximately and preferably between $10^3$ and $3 \times 10^6$ approximately.

Among the cationic polymers that may be mentioned more particularly are polymers of the polyamine, polyaminoamide and polyquaternary ammonium type. These are known products.

Among these polymers, mention may be made of:

(1) Homopolymers or copolymers derived from acrylic or methacrylic esters or amides and comprising at least one of the units of formulae (II) to (V) below:

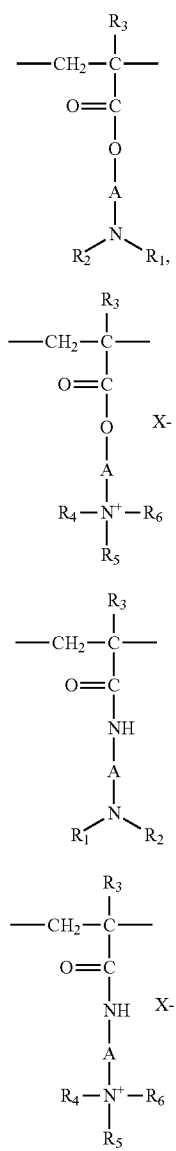

in which:

$R_3$, which may be identical or different, denotes a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

$X^-$ denotes an anion derived from a mineral or organic acid, such as a methosulfate anion or a halide, especially chloride or bromide.

The copolymers of family (1) can also contain one or more units derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulfate or with a dimethyl halide, the copolymers of acrylamide and of methacryloyloxyethyltrimethylammonium chloride described, for example, in patent application EP-A-080 976, the copolymers of acrylamide and of methacryloyloxyethyltrimethylammonium methosulfate, quaternized or non-quaternized vinylpyrrolidone/dialkylaminoalkyl acrylate or methacrylate copolymers. These polymers are described in detail in French patents 2 077 143 and 2 393 573, dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmethacrylamide copolymers, and crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name Salcare® SC 92 by the company Ciba. A crosslinked methacryloyl-oxy-ethyltrimethylammonium chloride homopolymer containing about 50% by weight of the homopolymer in mineral oil or in a liquid ester can also be used. These dispersions are sold under the names Salcare® SC 95 and Salcare® SC 96 by the company Ciba.

(2) Cyclopolymers of alkyldiallylamine or of dialkyldiallylammonium, such as the homopolymers or copolymers containing, as constituent of the chain, units corresponding to formula (VI) or (VII):

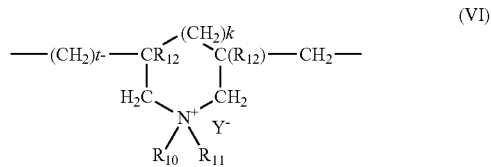

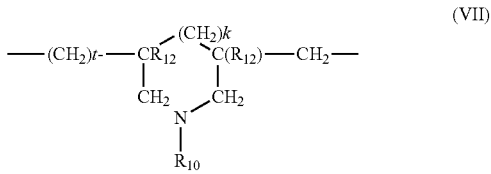

in which formulae k and t are equal to 0 or 1, the sum k+t being equal to 1; $R_{12}$ denotes a hydrogen atom or a methyl group; $R_{10}$ and $R_{11}$, independently of one another, denote an alkyl group having from 1 to 6 carbon atoms, a hydroxyalkyl group in which the alkyl group has preferably 1 to 5 carbon atoms, a lower ($C_1$-$C_4$) amidoalkyl group, or else $R_{10}$ and $R_{11}$ may, together with the nitrogen atom to which they are attached, denote heterocyclic groups, such as piperidyl or morpholinyl; $Y^-$ is an anion such as bromide, chloride, acetate, borate, citrate, tartrate, bisulfate, bisulfite, sulfate or phosphate. These polymers are especially described in French patent 2 080 759 and in its Certificate of Addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallylammonium salt (for example chloride) homopolymers sold especially under the name Merquat 100 by the company Nalco (and its homologues of low weight-average molar mass) and copolymers of diallyldimethylammonium chloride and of acrylamide.

(3) quaternary copolymers of vinyllactam (vinylpyrrolidone and/or vinylcaprolactam) and of vinylimidazole.

(4) The quaternary diammonium polymer containing repeating units corresponding to the formula (VIII):

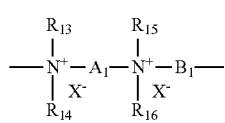
(VIII)

in which formula (VIII):

$R_{13}$, $R_{14}$, $R_{15}$ and $R_{16}$, which may be identical or different, represent aliphatic, alicyclic or arylaliphatic radicals containing from 1 to 20 carbon atoms or $C_1$-$C_6$ lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ represent polymethylene groups containing from 2 to 20 carbon atoms, which groups may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{13}$ and $R_{15}$ may form, with the two nitrogen atoms to which they are attached, a piperazine ring; in addition, if $A_1$ denotes a linear or branched, saturated or unsaturated alkylene or hydroxyalkylene group, $B_1$ may also denote a group $(CH_2)_n$—CO-D-OC—$(CH_2)_p$— in which:

n and p, which may be identical or different, are integers ranging from 2 to 20 approximately, D denotes:

a) a glycol residue of formula: —O—Z—O—, where Z denotes a linear or branched hydrocarbon-based radical or a group corresponding to one of the following formulae:

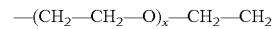

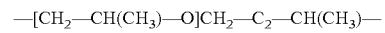

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

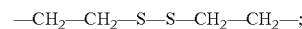

d) a ureylene group of formula: —NH—CO—NH—.

Preferably, X is an anion such as chloride or bromide.

These polymers generally have a number-average molecular weight of between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027, 020.

It is more particularly possible to use polymers that are formed essentially from repeating units corresponding to the formula:

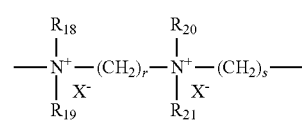
(a)

in which $R_{18}$, $R_{19}$, $R_{20}$ and $R_{21}$, which may be identical or different, denote an alkyl or hydroxyalkyl radical containing from 1 to 4 carbon atoms approximately, r and s are integers ranging from 2 to 20 approximately, and X is an anion derived from a mineral or organic acid.

One particularly preferred compound of formula (a) is that for which $R_{18}$, $R_{19}$, $R_{20}$ and $R_{21}$ represent a methyl radical and r=3, s=6 and X=Cl, which is called Hexadimethrine chloride according to INCI nomenclature (CTFA).

(5) Polyquaternary ammonium polymers composed of units of formula (IX):

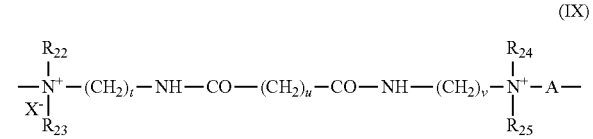
(IX)

in which formula (IX):

$R_{22}$, $R_{23}$, $R_{24}$ and $R_{25}$, which may be identical or different, represent a hydrogen atom or a methyl, ethyl, propyl, 3-hydroxyethyl, 3-hydroxypropyl or —CH$_2$CH$_2$(OCH$_2$CH$_2$)$_p$OH group, where p is equal to 0 or to an integer between 1 and 6, with the proviso that $R_{22}$, $R_{23}$, $R_{24}$ and $R_{25}$ do not simultaneously represent a hydrogen atom, t and u, which may be identical or different, are integers between 1 and 6, v is equal to 0 or to an integer between 1 and 34, X$^-$ denotes an anion such as a halide, A denotes a dihalide radical or preferably represents —CH$_2$—CH$_2$—O—CH$_2$—CH$_2$ Such compounds are described especially in Patent application EP-A-122 324.

Among these, mention may be made, for example, of the products Mirapol® A 15, Mirapol® AD1, Mirapol® AZ1 and Mirapol® 175, sold by the company Miranol.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, cationic cyclopolymers are preferably used, in particular the dimethyldiallylammonium chloride homopolymers sold under the name Merquat 100 by the company Nalco (and its homologues of low weight-average molar mass), polymers containing units of formula (VIII), and mixtures thereof.

According to the invention, the cationic polymer(s) (iii) with a cationic density of greater than 4 meq./g may represent from 0.01% to 10% by weight, preferably from 0.05% to 5% by weight and even more preferentially from 0.1% to 3% by weight relative to the total weight of the composition.

Preferably, the weight ratio of cationic polymers with a charge density of greater than or equal to 4 meq./g/polycondensate(s) of formula (A) ranges from 0.1 to 10, better still from 0.5 to 5 and even more preferentially from 0.5 to 1.

The composition according to the invention may optionally comprise synthetic or natural direct dyes, chosen from ionic or nonionic species, preferably cationic or nonionic species.

Examples of suitable direct dyes that may be mentioned include azo dyes; methine dyes; carbonyl dyes; azine dyes; nitro (hetero)aryl dyes; tri(hetero)arylmethane dyes; porphyrin dyes; phthalocyanin dyes, and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.0001% 20 to 10% by weight and preferably from 0.005% to 5% by weight of the total weight of the composition.

The medium that is suitable for dyeing, also known as the dye support, generally comprises water or a mixture of water and of one or more organic solvents other than the aromatic alcohol described previously, for example $C_1$-$C_4$ lower alkanols such as ethanol and isopropanol, polyols, for instance propylene glycol, dipropylene glycol, hexylene glycol or glycerol, and polyol ethers, for instance dipropylene glycol monomethyl ether.

According to one particular embodiment, the composition of the invention comprises a $C_1$-$C_4$ aliphatic alcohol, especially ethanol or isopropanol.

These solvents are generally present in proportions that may be between 1% and 40% by weight approximately and even more preferentially between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic (other than those that are useful in the invention), nonionic, amphoteric or zwitterionic polymers or mixtures thereof, mineral thickeners such as silicates or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 5 and 14 approximately and preferably greater than 5. According to one particular embodiment, the pH is between 6 and 11 approximately. It may be adjusted to the desired value by means of acidifying or basifying agents usually used in the dyeing of keratin fibres, or alternatively using standard buffer systems.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkaline carbonates, alkanolamines, such as mono-, di- and triethanolamines, and their derivatives, sodium hydroxide, potassium hydroxide and the compounds of formula (A) below:

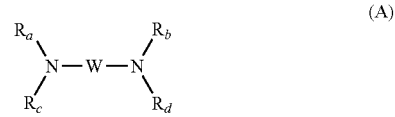

(A)

in which W is a propylene residue optionally substituted with a hydroxyl group or a $C_1$-$C_4$ alkyl radical; Ra, Rb, Rc and Rd, which may be identical or different, represent a hydrogen atom or a $C_1$-$C_4$ alkyl or $C_1$-$C_4$ hydroxyalkyl radical.

Advantageously, the composition according to the invention has a content of basifying agent(s) ranging from 0.01% to 30% by weight and preferably from 0.1% to 20% by weight relative to the weight of the composition.

According to one embodiment, the composition comprises at least one alkaline agent.

The composition according to the invention may comprise one or more oxidizing agents. Conventionally, the oxidizing agent is added to the composition at the time of use.

More particularly, the oxidizing agent(s) are chosen from hydrogen peroxide, urea peroxide, alkali metal bromates or ferricyanides, peroxygenated salts, for instance alkali metal or alkaline-earth persulfates, perborates and percarbonates, and also peracids and precursors thereof.

Advantageously, the oxidizing agent is hydrogen peroxide.

The content of oxidizing agent(s) more particularly represents from 0.1% to 20% by weight and preferably from 0.5% to 10% by weight relative to the weight of the composition.

Preferably, the oxidizing agent is hydrogen peroxide in aqueous solution, the concentration of which ranges, more particularly, from 0.1% to 50% by weight, more particularly between 0.5% and 20% by weight and even more preferentially between 1% and 15% by weight relative to the weight of the oxidizing composition.

Preferably, the composition of the invention before mixing with the oxidizing agent is in liquid form at a temperature of 25° C. and at atmospheric pressure (760 mmHg), i.e. it is capable of flowing under the action of its own weight.

Preferably, the viscosity at a temperature of 25° C. and at a shear rate of 1 s$^{-1}$ of the composition of the invention before mixing with the oxidizing agent is between 10$^{-2}$ Pa·s and 5 Pa·s and preferably between 10$^{-1}$ Pa·s and 2 Pa·s. It may be measured using a Thermo Haake RS600 rheometer with cone-plate geometry or an equivalent machine.

Preferably, the composition of the invention before mixing with the oxidizing agent contains a total amount of ionic or nonionic surfactants of greater than 8% and even more preferentially greater than 10%.

The dyeing process according to the invention thus consists in mixing a composition free of oxidizing agent, comprising at least one dye precursor, at least one polycondensate of polyethylene and polypropylene as defined previously, and at least one cationic polymer with a charge density of greater than or equal to 4 meq./g, and optionally an alkaline agent, with a composition comprising an oxidizing agent, and in applying this composition to wet or dry human keratin fibres.

The composition is then left in place for a time usually ranging from one minute to one hour and preferably from 5 minutes to 30 minutes.

The temperature during the process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

EXAMPLES

The following compositions were prepared:

| | % by weight (AM) |
|---|---|
| Composition A | |
| 1,4-Diaminobenzene | 0.36 |
| 2-Methyl-1,3-dihydroxybenzene | 0.15 |
| 1,3-Dihydroxybenzene | 0.77 |
| 6-Hydroxyindole | 0.07 |
| 1-Hydroxy-3-aminobenzene | 0.41 |
| Rapeseed fatty acid amide 4 OE (PEG-4 rapeseed amide) | 8.12 |
| Decyl alcohol 3 OE (Deceth-3) | 6.93 |
| Monoglycerolated lauryl alcohol (glyceryl lauryl ether) | 7 |
| Oleyl alcohol | 1.1 |
| Laureth-5 carboxylic acid | 4.5 |
| Ethanolamine | 3.66 |
| EDTA | 0.2 |
| Ethanol | 8.2 |
| Propylene glycol | 6.2 |
| Hexylene glycol | 3 |
| Dipropylene glycol | 3 |
| POE/POP/POE (Poloxamer 338 sold by BASF; a = a' = 128 b = 54) | 2 |
| Polyquaternium-6 (cationic polymer according to the invention) Polydimethyldiallylammonium chloride at 40% in water | 1.36 |
| Ammonium thiolactate | 0.464 |
| Erythorbic acid | 0.12 |
| Ammonium hydroxide | 2.88 |
| Water | qs 100 |
| Composition B | |
| 1,4-Diaminobenzene | 0.36 |
| 2-Methyl-1,3-dihydroxybenzene | 0.15 |
| 1,3-Dihydroxybenzene | 0.77 |
| 6-Hydroxyindole | 0.07 |
| 1-Hydroxy-3-aminobenzene | 0.41 |
| Rapeseed fatty acid amide 4 OE (PEG-4 rapeseed amide) | 8.12 |
| Decyl alcohol 3 OE (Deceth-3) | 6.93 |
| Monoglycerolated lauryl alcohol (glyceryl lauryl ether) | 7 |
| Oleyl alcohol | 1.1 |
| Laureth-5 carboxylic acid | 4.5 |
| Ethanolamine | 5.66 |
| EDTA | 0.2 |
| Ethanol | 8.2 |
| Propylene glycol | 6.2 |
| Hexylene glycol | 3 |
| Dipropylene glycol | 3 |
| POE/POP/POE (Poloxamer 338 sold by BASF) a = a' = 128 b = 54) | 2 |
| Polyquaternium-6 (cationic polymer according to the invention) polydimethyldiallylammonium chloride | 1.36 |
| Thiolactic acid | 0.251 |
| Erythorbic acid | 0.12 |
| Water | qs 100 |
| Composition C | |
| 1,4-Diaminobenzene | 0.36 |
| 2-Methyl-1,3-dihydroxybenzene | 0.15 |
| 1,3-Dihydroxybenzene | 0.77 |
| 6-Hydroxyindole | 0.07 |
| 1-Hydroxy-3-aminobenzene | 0.41 |
| Rapeseed fatty acid amide 4 OE (PEG-4 rapeseed amide) | 8.12 |
| Decyl alcohol 3 OE (Deceth-3) | 6.93 |
| Monoglycerolated lauryl alcohol (glyceryl lauryl ether) | 7 |
| Oleyl alcohol | 1.1 |
| Laureth-5 carboxylic acid | 4.5 |
| Ethanolamine | 5.66 |
| EDTA | 0.2 |
| Ethanol | 8.2 |
| Propylene glycol | 6.2 |
| Hexylene glycol | 6 |
| POE/POP/POE (Poloxamer 338 sold by BASF; a = a' = 128 b = 54) | 2 |
| Polyquaternium-6 | 1.36 |
| Thiolactic acid | 0.251 |
| Erythorbic acid | 0.12 |
| Water | qs 100 |

Compositions A, B and C are stable over time. Each of them is mixed with 1.5 times its own weight of an oxidizing composition comprising 7.5% hydrogen peroxide at pH 2. The mixtures obtained apply easily to dark chestnut-brown hair, without running.

After a leave-on time of 30 minutes at 25° C. followed by rinsing, the hair is washed and dried. The head of hair is then uniformly dyed in a strong golden light chestnut-brown colour with the two mixtures obtained from compositions A, B and C.

The invention claimed is:

1. A hair dye composition comprising:
   at least one oxidation dye precursor;
   at least one polycondensate of ethylene oxide and propylene oxide of formula

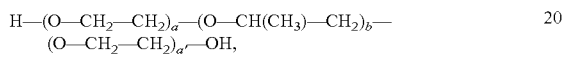

wherein a and a' range from 2 to 150 and b ranges from 1 to 100; and
   at least one cationic polymer with a charge density of greater than or equal to 4 meq./g.

2. A hair dye composition according to claim 1, wherein the at least one oxidation dye precursor is at least one oxidation base chosen from para-phenylenediamines, bis(phenyl)alkylenediamines, para-aminophenols, ortho-aminophenols, heterocyclic bases, and the addition salts thereof, and optionally at least one coupler chosen from meta-phenylenediamines, meta-aminophenols, meta-diphenols, naphthalene-based couplers, heterocyclic couplers, and the addition salts thereof.

3. The hair dye composition according to claim 1, wherein for the at least one polycondensate of ethylene oxide and propylene oxide, a and a' range from 10 to 130 and b ranges from 20 to 80.

4. The hair dye composition according to claim 1, wherein for the at least one polycondensate of ethylene oxide and propylene oxide, a and a' range from 50 to 130 and b ranges from 30 to 80.

5. The hair dye composition according to claim 1, wherein for the at least one polycondensate of ethylene oxide and propylene oxide, a and a' range from 80 to 130 and b ranges from 40 to 80.

6. The hair dye composition according to claim 1, wherein for the at least one polycondensate of ethylene oxide and propylene oxide, a and a' are identical.

7. The hair dye composition according to claim 1, wherein the amount of the at least one polycondensate of ethylene oxide and propylene oxide ranges from about 0.1% to about 20% by weight, relative to the total weight of the composition.

8. The hair dye composition according to claim 1, wherein the amount of the at least one polycondensate of ethylene oxide and propylene oxide ranges from about 1% to about 5% by weight, relative to the total weight of the composition.

9. The hair dye composition according to claim 1, wherein the at least one cationic polymer with a charge density of greater than or equal to 4 meq./g is chosen from:
   (1) homopolymers and copolymers derived from acrylic or methacrylic esters or amides and comprising at least one of formulae (II) to (V):

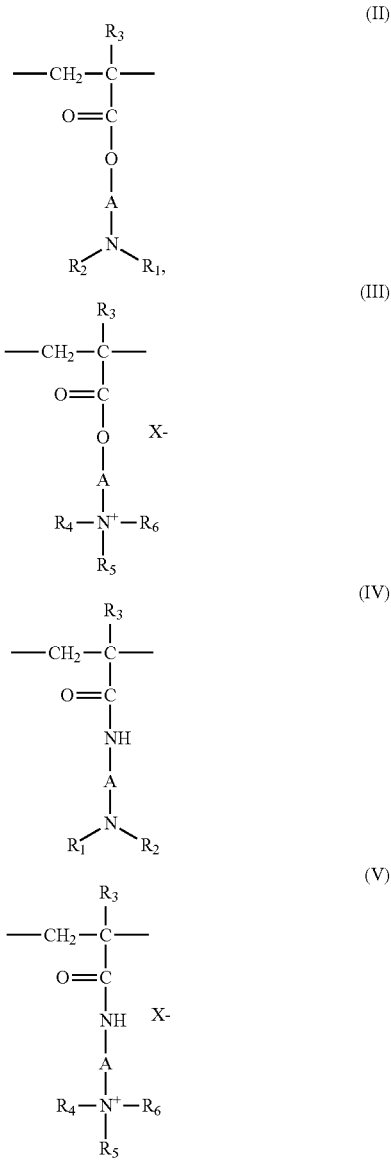

wherein:

$R_3$, which may be identical or different, is chosen from hydrogen atoms and $CH_3$ radicals;

A, which may be identical or different, is chosen from linear and branched alkyl groups of 1 to 6 carbon atoms and hydroxyalkyl groups of 1 to 4 carbon atoms;

$R_4$, $R_5$ and $R_6$, which may be identical or different, are chosen from alkyl groups containing from 1 to 18 carbon atoms and benzyl radicals;

$R_1$ and $R_2$, which may be identical or different, are chosen from hydrogen and alkyl groups containing from 1 to 6 carbon atoms;

$X^-$ is chosen from anions derived from mineral or organic acids;

(2) cyclopolymers of alkyldiallylamine and cyclopolymers of dialkyldiallylammonium (3) quaternary polymers of vinylpyrrolidone and of vinylimidazole;

(4) quaternary diammonium polymers containing repeating units of formula (VIII):

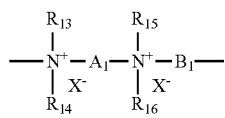
(VIII)

wherein in formula (VIII):

$R_{13}$, $R_{14}$, $R_{15}$ and $R_{16}$, which may be identical or different, are chosen from aliphatic, alicyclic and arylaliphatic radicals containing from 1 to 20 carbon atoms, $C_1$-$C_6$ lower hydroxyalkylaliphatic radicals, linear and branched $C_1$-$C_6$ alkyl radicals substituted by a nitrile, ester, acyl, amide, —CO—O—$R_{17}$-D, or —CO—NH—$R_{17}$-D group, wherein $R_{17}$ is an alkylene and D is a quaternary ammonium group, or $R_{13}$, $R_{14}$, $R_{15}$ and $R_{16}$, together or separately, constitute, with the nitrogen atoms to which they are attached, heterocycles optionally containing a second heteroatom other than the nitrogen;

$A_1$ and $B_1$ are chosen from polymethylene groups containing from 2 to 20 carbon atoms, which may be linear or branched and saturated or unsaturated and optionally comprise, joined to or intercalated in the main chain, at least one aromatic ring, at least one oxygen atom, at least one sulfur atom, and sulfoxide, sulfone, disulfide, amino, alkylamino, hydroxyl, quaternary ammonium, ureido, amide and ester groups; and $X^-$ is chosen from anions derived from mineral or organic acids; wherein $A_1$, $R_{13}$ and $R_{15}$ may form, with the two nitrogen atoms to which they are attached, a piperazine ring; and further wherein, if $A_1$ is a saturated or unsaturated, linear or branched alkylene or hydroxyalkylene radical, $B_1$ may be chosen from $(CH_2)_n$—CO-D-OC—$(CH_2)_p$— groups wherein:

n and p, which may be identical or different, are chosen from integers ranging from about 2 to about 20, and D is chosen from:

a) a glycol residue of formula: —O—Z—O—, where Z is chosen from linear and branched hydrocarbon-based radicals and groups of one of the formulae:

—(CH$_2$—CH$_2$—O)x-CH$_2$—CH$_2$— and

—[CH$_2$—CH(CH$_3$)—O]y-CH$_2$—CH(CH$_3$)— where x and y are chosen from integers from 1 to 4, representing a defined and unique degree of polymerization and numbers from 1 to 4 representing an average degree of polymerization;

b) a bis-secondary diamine residue;

c) a bis-primary diamine residue of formula: —NH—Y—NH—, where Y is chosen from linear and branched hydrocarbon-based radicals and divalent radicals

—CH$_2$—CH$_2$—S—S—CH$_2$—CH$_2$—;

d) a ureylene group of formula: —NH—CO—NH—;

(5) polyquaternary ammonium polymers of formula (IX):

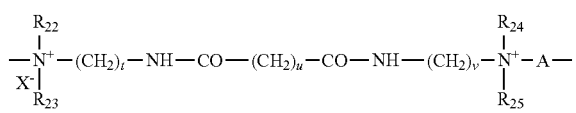
(IX)

wherein:

$R_{22}$, $R_{23}$, $R_{24}$ and $R_{25}$, which may be identical or different, are chosen from hydrogen atoms and methyl, ethyl, propyl, β-hydroxyethyl, β-hydroxypropyl and —CH$_2$CH$_2$(OCH$_2$CH$_2$)$_p$OH radicals, wherein p is chosen from 0 and integers ranging from 1 and 6, with the proviso that $R_{22}$, $R_{23}$, $R_{24}$ and $R_{25}$ do not simultaneously represent a hydrogen atom, t and u, which may be identical or different, are chosen from integers ranging from 1 and 6, v is chosen from 0 and integers ranging from 1 and 34, $X^-$ is an anion, and A is chosen from radicals of a dihalide and —CH$_2$—CH$_2$—O—CH$_2$—CH$_2$;

(6) polyalkyleneimines, polymers comprising vinylpyridine units, polymers comprising vinylpyridinium units, condensates of polyamines and of epichlorohydrin, quaternary polyureylenes, and chitin derivatives.

10. The hair dye composition according to claim 9, wherein the cyclopolymers of alkyldiallylamine and, . . . are chosen from the homopolymers and copolymers comprising, as constituent of the chain, at least one unit chosen from formula (VI) and (VII):

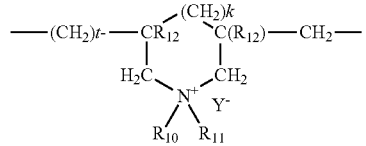
(VI)

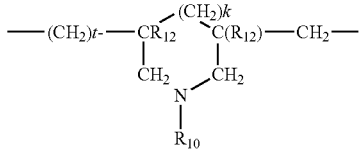
(VII)

wherein k and t are chosen from 0 and 1, the sum k+t being 1; $R_{12}$ is chosen from hydrogen atoms and methyl groups; $R_{10}$ and $R_{11}$, independently of one another, are chosen from alkyl groups having from 1 to 6 carbon atoms, hydroxyalkyl groups, and lower ($C_1$-$C_4$) amidoalkyl groups, or $R_{10}$ and $R_{11}$ are, together with the nitrogen atom to which they are attached, chosen from heterocyclic groups; and $Y^-$ is an anion.

11. The hair dye composition according to claim 1, wherein the at least one cationic polymer with a charge density of greater than or equal to 4 meq./g is chosen from cationic cyclopolymers and polymers containing units of formula (VIII).

12. The hair dye composition according to claim 1, wherein the at least one cationic polymer with a charge density of greater than or equal to 4 meq./g is present in an amount ranging from about 0.01% to about 10% by weight, relative to the total weight of the composition.

13. The hair dye composition according to claim 1, wherein the at least one cationic polymer with a charge density of greater than or equal to 4 meq./g is present in an amount ranging from about 0.1% to about 3% by weight, relative to the total weight of the composition.

14. The hair dye composition according to claim 1, wherein the weight ratio of the at least one cationic polymer with a charge density of greater than or equal to 4 meq./g to the at least one polycondensate of ethylene oxide and propylene oxide ranges from about 0.1 to about 10.

15. The hair dye composition according to claim 1, wherein the weight ratio of the at least one cationic polymer with a charge density of greater than or equal to 4 meq./g to the at least one polycondensate of ethylene oxide and propylene oxide ranges from about 0.5 to about 1.

16. The hair dye composition according to claim 1, wherein the dye composition is liquid at about 25° C. and at atmospheric pressure (760 mmHg).

17. The hair dye composition according to claim 1, further comprising a total amount of ionic and nonionic surfactants of greater than about 8%.

18. The hair dye composition according to claim 1, further comprising at least one oxidizing agent.

19. A process for dyeing hair, said process comprising:
(i) mixing at least one oxidizing agent and a dye composition comprising:
at least one oxidation dye precursor; at least one polycondensate of ethylene oxide and propylene oxide of formula

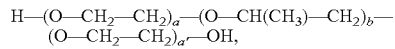

wherein a and a' range from 2 to 150 and b ranges from 1 to 100; and at least one cationic polymer with a charge density of greater than or equal to 4 meq./g; and
(ii) applying the resultant mixture to hair.

20. A two-compartment device comprising:
(i) in a first compartment, a first composition comprising a dye composition comprising at least one oxidation dye precursor; at least one polycondensate of ethylene oxide and propylene oxide of formula

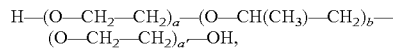

wherein a and a' range from 2 to 150 and b ranges from 1 to 100; and at least one cationic polymer with a charge density of greater than or equal to 4 meq./g; and,
(ii) in a second compartment, a second composition comprising at least one oxidizing agent.

* * * * *